United States Patent [19]

Jacobson

[11] Patent Number: 5,268,508

[45] Date of Patent: Dec. 7, 1993

[54] METHOD FOR MANUFACTURING 3-AMINO-2-CYCLOHEXENE-1-ONE, AND A NOVEL POLYMER INGREDIENT AND ITS PREPARATION

[75] Inventor: Stephen E. Jacobson, Princeton Junction, N.J.

[73] Assignee: E. I. Du Pont de Nemours and Company, Wilmington, Del.

[21] Appl. No.: 929,904

[22] Filed: Aug. 17, 1992

Related U.S. Application Data

[62] Division of Ser. No. 685,359, Apr. 15, 1991, Pat. No. 5,149,874.

[51] Int. Cl.$^5$ .......................................... C07C 249/02
[52] U.S. Cl. .................................................. 564/248
[58] Field of Search ................................ 564/248, 462

[56] References Cited

U.S. PATENT DOCUMENTS

| | | | |
|---|---|---|---|
| 2,421,937 | 6/1947 | Haury | 260/566 |
| 2,425,185 | 8/1947 | Haury | 167/24 |
| 3,435,072 | 3/1969 | Kabas | 260/566 |
| 3,975,285 | 8/1976 | Ohnishi et al. | 252/299 |

FOREIGN PATENT DOCUMENTS

| | | | |
|---|---|---|---|
| 1262999 | 3/1968 | Fed. Rep. of Germany | 564/248 |
| 2135451 | 6/1987 | Japan . | |

OTHER PUBLICATIONS

Murahashi et al., "Catalytic Alkyl Group Exchange, etc." *J. Am. Chem. Soc.* (1983), 105, 5002–5011.
Solomons, T., "*Organic Chemistry*", 2nd Ed., John Wiley and Sons, New York, 1980.
*Journal of American Chemical Society*, 108, 862 (1986).

*Primary Examiner*—Allen J. Robinson
*Assistant Examiner*—P. O'Sullivan

[57] ABSTRACT

A method of manufacturing 3-amino-2-cyclohexene-1-one by hydrogenating m-phenylenediamene to produce a novel intermediate salt of 3-amino-2-cyclohexene-1-imine followed by hydrolysis to produce 3-amino-2-cyclohexene-1-one. The novel intermediate 3-amino-2-cyclohexene-1-imine has also be isolated.

5 Claims, No Drawings

METHOD FOR MANUFACTURING 3-AMINO-2-CYCLOHEXENE-1-ONE, AND A NOVEL POLYMER INGREDIENT AND ITS PREPARATION

This is a division of application Ser. No. 07/685,359, filed Apr. 15, 1991, now U.S. Pat. No. 5,149,874.

FIELD OF THE INVENTION

This invention relates to a method of manufacturing a polyfunctional intermediate 3-amino-2-cyclohexene-1-one (ACO), and, more particularly, a method whereby a concentrated solution of m-phenylenediamene (MPD) in acid is hydrogenated in the presence of a palladium or platinum catalyst or mixtures thereof to produce a novel bifunctional intermediate acid salt of 3-amino-2-cyclohexene-1-imine (ACI) followed by hydrolysis to produce 3-amino-2-cyclohexene-1-one. During the process it is also possible to isolate the novel bifunctional intermediate, ACI.

DESCRIPTION OF RELATED ART

Japanese Kokai Patent No. SHO 62 [1987]- 135451 describes a method for manufacturing 3-amino-2-cyclohexene-1-one whereby m-phenylenediamine (<5%) in 4% aqueous acetic acid is simultaneously hydrogenated and hydrolysed in the presence of water and a reduction catalyst (1 part catalyst to 5.4 parts m-phenylenediamine). The product is isolated by extraction with an organic solvent, which after removal produces crystals in 58% yield Naturwissenshaften 47, 83 (1960) describes the manufacture of ACO by condensing ammonia with dihydroresorcinol followed by dehydration. Dihydroresorcinol is an expensive starting material and is not a large scale object-of-commerce. Therefore, the process may not be practical from an industrial point of view.

SUMMARY OF THE INVENTION

One aspect of the invention relates to an economically and commercially practicable synthesis of ACO comprising to the steps of:
(a) hydrogenating a concentrated solution of m-phenylenediamine in acid in the presence of a reduction catalyst at an elevated hydrogen pressure and at a temperature of about 25° C. to about 90° C. to produce an acid salt of 3-amino-2-cyclohexene-1-imine;
(b) hydrolyzing said salts of 3-amino-2-cyclohexene-1-imine at a pH of 12 or greater and at a temperature ranging from about ambient temperature to about 80° C.; and
(c) precipitating and recovering 3-amino-2-cyclohexene-1-one.

Another aspect of the invention relates to the discovery of a novel intermediate, 3-amino-2-cyclohexene-1-imine and its salts.

A further aspect of the invention relates to a method of preparing a salt of ACI by the partial hydrogenation of MPD in acidic solution in the presence of a platinum or palladium catalyst or mixtures thereof. The solvent is removed by evaporation to recover the acid salt of the novel compound, ACI.

DETAILED DESCRIPTION OF THE INVENTION

The present invention may be described by the following general equation:

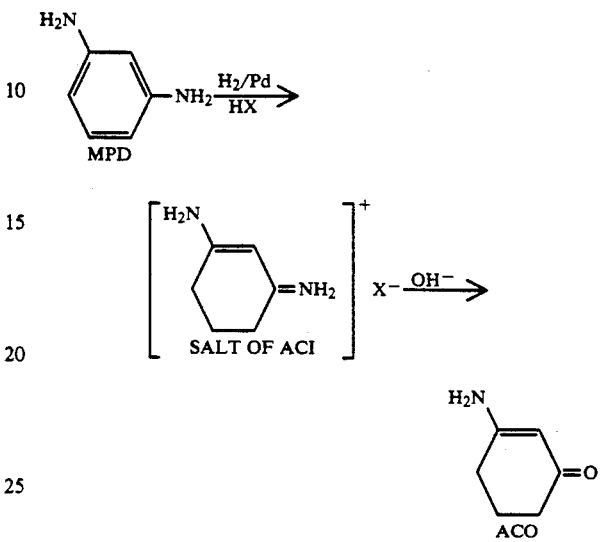

It is the object of this invention to provide a convenient low cost process for 3-amino-2-cyclohexene-1-one which gives improved yields over the prior art and requires a minimum amount of environmentally unacceptable isolation solvents. The compounds, 3-amino-2-cyclohexene-1-one (ACO), and its substituted derivatives are valuable intermediates for the preparation of dyes, pharmaceuticals, agricultural chemicals and polymer intermediates. Another object of the invention is to isolate the previously unknown imine derivative, 3-amino-2-cyclohexene-1-imine, as a precursor to new valuable products, such as drugs, agricultural products and polymer intermediates.

One aspect of the invention is the manufacture of ACO. First, a concentrated solution of m-phenylenediamine (>20%) in acid is hydrogenated at an elevated hydrogen pressure in the presence of a reduction catalyst, e.g., 1 part metal on a support to 800 part MPD at 25°-90' C.

Catalysts include platinum and palladium or mixtures thereof which may or may not be on a support such as carbon, alumina, barium carbonate, steam activated peat carbon or the like. Good yields are obtained with a 5% palladium on carbon at a concentration of 0.001 to 0.01 mole per mole of MPD. Catalyst concentrations of from 0.001 to 5% may be used. It will be appreciated by those skilled in the art that at lower concentrations the reaction is slow and at higher concentrations the cost of the catalyst greatly affects the process economics.

The hydrogenation of MPD is carried out under elevated pressure. Good results can be obtained at a hydrogen pressure of 50-500 psig, the preferred pressure depending on the equipment limitations and availability. Acceptable rates can be obtained at modest pressures which makes the process practical. The temperature of the hydrogenation reaction can range from 25°-90° C., generally 40°-60° C.

Typically the reaction is conducted under concentrated conditions in a solvent or solvent mixture such as organic or mineral acids diluted with water, alcohols or other miscible solvents. The preferred solvent is 50–80% aqueous acetic acid. The minimum concentration of acetic acid is 15%, the maximum is 100%. Other carboxylic acids such as propionic and butyric can be used as well as mineral acids such as HCl, HBr, $HClO_4$ and $H_3PO_4$. With mineral acids or carboxylic acids at least one equivalent of acid per mole of m-phenylenediamine is required, although greater amounts can be beneficial.

The solution is cooled externally or by cooling coils to ambient temperature and the catalyst removed by standard techniques, such as filtration or centrifugation. The solution contains ACI as its acid salt. In order to hydrolyze the imine to the ketone, it is necessary to adjust the pH to about 12–14 with the range of about 13.5–14 preferred. Alkali metal bases such as sodium, lithium or potassium hydroxides can be used. Potassium hydroxide is a preferred base because of the greater solubility of its acetate salt. The temperature of the hydrolysis reaction can range from about ambient temperature to about 80° C., with 40°–60° C. preferred. After hydrolysis and cooling the product, ACO precipitates and is isolated and dried at temperatures up to 100° C. to avoid thermal decomposition. Yields of ACO in excess of 85% can be obtained after filtraton and drying.

Advantages of the invention include higher volumetric efficiency, i.e., greater than 10 times the concentation creating a more economical process Further, less than ⅓ the amount of catalyst is required in conjunction with a reaction rate increase by more than three-fold. Also, the desired product precipitates from the reaction solution allowing isolation by, for example, filtration, which eliminates extraction methods of the prior art which may be costly, inefficient, and from which the solvent must be disposed in an environmentally safe manner.

Another aspect of the invention resides in the discovery of a novel intermediate ACI, which in the form of its various salts or the neutral compound is a novel polyfunctional compound which can be used in the synthesis of precursors for pharmaceuticals, agricultural chemicals and polymer intermediates.

A further aspect of the invention is the method for preparing the acid salt of ACI comrising the partial hydrogenation of MPD in acidic solution in the presence of a reduction catalyst. After the partial hydrogenation, the solvent is removed by evaporation, and the remaining product is the acid salt of the intermediate compound, ACI.

The following examples serve to illustrate the invention, but are not intended to limit the scope of the invention.

EXAMPLE 1

The process for synthesis of 3-amino-2-cyclohexene-1-one is illustrated by the following procedure. A one liter agitated autoclave was charged with m-phenylenediamine (162.2 g, 1.5 moles), acetic acid (180 g, 3.0 moles), water (225 g) and 5% palladium on carbon, 55% in water (4.8 g) and purged with nitrogen. Hydrogen was added by pressuring at 140 psig for 3 hours at 60° C. The reaction was cooled to room temperature, vented, and the catalyst was removed by standard methods. The clarified reaction mass was cooled to 0° C. and powdered potassium hydroxide (177 g, 3.1 moles) was added slowly. The agitated mixture was heated to 50° C. and held two hours and then cooled to room temperature. The precipated product was filtered and dried under vacuum. The yield was 145.1 g (1.3 moles, 87% theory of 3-amino-2-cyclohexene-1-one).

EXAMPLE 2

The reaction described in Example 1 was repeated except hydrochloric acid (37%) replaced acetic acid in a 1:1 molar ratio with m-phenylenediamine and the solution was heated at 60° C. for 6 hours. Also, sodium hydroxide (50% in water) replaced the powdered potassium hydroxide in Example 1. The hydrolysis solution was reacted at 60° C. for 0.5 hour and the volume reduced under vacuum until a pink solid precipitated. The crude solid was then extracted with hot acetonitrile, filtered, and cooled to yield pure 3-amino-2-cyclohexene-1-one (43% yield).

EXAMPLE 3

The reaction described in Example 1 was repeated except m-phenylenediamine was hydrogenated at 70° C. under 420 psig hydrogen pressure for 3.5 hours (88% GC yield of 3-amino-2-cyclohexene-1-one). Hydrolysis resulted in a 80% isolated yield of 3-amino-2-cyclohexene-1-one.

EXAMPLE 4

The reaction described in Example 1 was repeated except a 5% palladium on barium carbonate catalyst was used for the m-phenylenediamine hydrogenation resulting in a 70% GC yield of the acetate salt of 3-amino-2-cyclohexene-1-imine and 29% m-phenylenediamine remaining. On hydrolysis, a 62% isolated yield of 3-amino-2-cyclohexene-1-one was obtained.

EXAMPLE 5

The reaction described in Example 1 was repeated except a 5% palladium on alumina catalyst was used for m-phenylenediamine hydrogenation (62% GC yield of the acetate salt of 3-amino-2-cyclohexene-1-imine and 7% m-phenylenediamine remaining). On hydrolysis a 55% yield of 3-amino-2-cyclohexene-1-one was isolated.

EXAMPLE 6

The reaction described in Example 1 was repeated except a 10% platinum on activated carbon catalyst was used for m-phenylenediamine hydrogenation (63% GC yield of the acetate salt of 3-amino-2-cyclohexene-1-imine and 17% unreacted m-phenylenediamine). An isolated yield of 55% yield of 3-amino-2-cyclohexene-1-one was obtained.

EXAMPLE 7

The reaction described in Example 1 was repeated except a 1%Pd-0.05%Pt on silica catalyst, as described in co-pending application, Ser. No. 07/587,879, was used for m-phenylenediamine hydrogenation (44% GC yield of the acetate salt of 3-amino-2-cyclohexene-1-imine and 33% unreacted m-phenylenediamine). An isolated yield of 39% yield of 3-amino-2-cyclohexene-1-one was obtained.

EXAMPLE 8

The reaction described in Example 1 was repeated except no water was used in the hydrogenation mixture (67% GC yield of the acetate salt of 3-amino-2-cyclohexene-3-imine and 23% remaining m- phenylenediamine after 5.5 hours of hydrogenation). A 58% yield of 3-amino-2-cyclohexene-1-one was isolated after hydrolysis with 50% sodium hydroxide as in Example 2.

EXAMPLE 9

The reaction described in Example 1 was repeated except a 1:1 molar ratio of m-phenylenediamine:acetic acid was reacted for 4.5 hours to give a 86% GC yield of the acetate salt of 3-amino-2-cyclohexene-1-imine and 14% remaining m-phenylenediamine. Hydrolysis resulted in a 75% isolated yield of 3-amino-2-cyclohexene-1-one.

EXAMPLE 10

The reaction described in Example 1 was repeated except the m-phenylenediamine was reacted with hydrogen at 50° C. for 6 hours to give an 84% yield of the acetate salt of 3-amino-2-cyclohexene-1-imine. On hydrolysis a 77% isolated yield of 3-amino-2-cyclohexene-1-one was obtained.

EXAMPLE 11

The reaction described in Example 1 was repeated except the water was replaced with ethanol A 42% GC yield of the acetate salt of 3-amino-2-cyclohexene-1-imine was obtained. A 34% isolated yield of 3-amino-2-cyclohexene-1-one was obtained on hydrolysis.

EXAMPLE 12

The reaction described in Example 1 was repeated except an equimolar ratio of phosphoric acid (in place of hydrochloric acid) and m-phenylenediamine were reacted at 50° C., 140 psig hydrogen to give a GC yield of 32% phosphate salt of 3-amino-2-cyclohexene-1-imine and 62% unreacted m-phenylenediamine. Hydrolysis yielded a 25% yield of 3-amino-2-cyclohexene-1-one.

EXAMPLE 13

The reaction described in Example 1 was repeated except used 20% palladium on steam activated peat carbon (1.6 g) and reacted the m-phenylenediamine with hydrogen (140 psig) for 1.5 hours to give a 97% GC yield of the acetate salt of 3-amino-2-cyclohexene-1-imine. Hydrolysis gave a 91% isolated yield on 3-amino-2-cyclohexene-1-one.

EXAMPLE 14

Hydrolysis Example at pH 11

The hydrogenation of m-phenylenediamine was carried out under the conditions of Example 1 to give a 93% yield of the acetate salt of 3-amino-2-cyclohexene-1-imine. A solution of 50% sodium hydroxide was added until the pH was 11 (20 g). The resulting solution was heated for three hours at 50° C. and two hours at 75C. A GC analysis showed a 3% yield of 3-amino-2-cyclohexene-1-one and 91% of the acetate of 3-amino-2-cyclohexene-1-imine remaining after three hours and 8% and 85%, respectively, after the total five hours.

This experiment demonstrates the importance of a very high pH (pH=14) for efficient hydrolysis to 3-amino-2-cyclohexene-1-one.

EXAMPLE 15

Preparation of the Acetate Salt of 3-Amino-2-cyclohexene-1-imine

After partial hydrogenation of m-phenylenediamine as detailed in Example 1, the aqueous acetic acid solution was removed under vacuum at 80° C. The resulting viscous oil was dissolved in a mixture of ethanol (150 g) and acetonitrile (700 g) to precipitate a white crystalline solid of the acetate salt of 3-amino-2-cyclohexene-1-imine (146 g, 57% yield) Melting Point=159°-162° C.

300 MHz $^1$H NMR (TMS standard, DMSO-D$_6$ solvent) 1.65 γ(singlet, 3.0, CH$_3$CO$_2$); 1.75 γ(pentuplet, 2.0, CH$_2$CH$_2$CH$_2$); 2.43γ(triplet, 4.0, CH$_2$CH$_2$CH$_2$); 5.47γ(singlet, 1.0, =CH); 9.31γ(multiplet, 4.0, =NH$_2$) 75 MHz $^{13}$C NMR (TMS reference) with the following assignments:

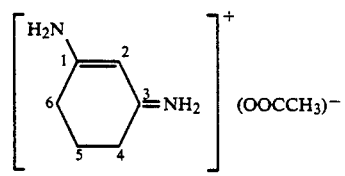

20.43γ, $^1$J(C-H)=130.8 (triplet), 1.0,C-5; 25.43γ, $^1$J(C-H)=124.6 (quartet), 1.0, CH$_3$; 27.64γ, $^1$J(C-H)=127.4 (multiplet), 2.0, C-4,C-6; 89.88γ, $^1$J(C-H)=159.7 (doublet), 1.0, C-2; 173.20γ,$^2$J(C-H)= 5.57(multiplet), 2.0, C-1, C-3; 174.32γ,$^2$J(C-H)=5.70(quartet), 1.0, C(O).

Elemental Analyses: Experimental, %C=55.98, %H=8.34, %N=16.70; Calculated, %C=56.44, %H=8.31, N=16.46.

EXAMPLE 16

Preparation of the Hydrochloride Salt of 3-Amino-2-cyclohexene-1-imine

A one liter autoclave equipped with an overhead stirrer and a thermocouple was charged with m-phenylenediamine (33.0 g, 0.3 mole), 37% aqueous hydrochloric acid (29.6 g, 0.3 mole), water (358 g), and 5% palladium on carbon (1.2 g, 50% in water). After closing the autoclave, it was purged with nitrogen and then pressured with hydrogen at 140 psig for 6.0 hours at 50° C. The reaction was then cooled to room temperature, vented and filtered. The solution was then rotovapped to dryness at 70° C.

The crude solid was recrystallized from hot ethanol solution to give a pink crystalline solid (13.2 g, 37% yield).

300 MHz $^1$NMR (TMS standard, DMSO-D$_6$) 1.77γ(pentuplet, 2.0, CH$_2$CH$_2$CH$_2$; 2.46γ(triplet, 4.0, CH$_2$CH$_2$CH$_2$); 5.56 γ(singlet, 1.0, =CH); 8.758 γ(singlet, 2.0, =NH$_2$); 9.03γ(singlet, 2.0, =NH$_2$).

75 MHz $^{13}$C NMR (TMS reference, DMSO-D$_6$ solvent) with the following assignments: 20.30γ, $^1$J(C-H)=130.8, 1.0, C-5, 27.56γ, $^1$J(C-H)=129.5, 2.0, C-4, C-6, 89.80 , $^1$J(C-H)=160.8, 1.0, C-2, 173.64 , 2.0, C-1, C-3.

Elemental Analysis: Experimental, %C=48.07, %H=7.73, %N=19.30, %Cl=24.43; Calculated, %C=49.15, %H=7.58, %N=19.10, %Cl=24.42.

EXAMPLE 17

Preparation of 3-Amino-2-cyclohexene-1-imine

The acetate salt of 3-amino-2-cyclohexene-1-imine (5.0 g, 29 m/mol) was dissolved in methanol (25 ml) in a 25 ml round bottomed flask equipped with a nitrogen inlet, condenser, thermometer, and magnetic stirrer. The solution was purged with nitrogen for ten minutes. Then sodium methoxide (2.7 g, 50 m/mol) was added to the solution. The solution was stirred for three hours at room temperature under nitrogen. The solvent was then removed under vacuum at 60° C.

The solid was then extracted with dichloromethane (4-20 ml portions) and the solution evaporated to dryness. The yellow solid was recrystallized from hot toluene to give yellow crystals. The crystals were dried at 60° C. in an oven under vacuum (0.81 g, 26% yield). Melting point = 112°-118° C.

300 MHz $^1$H NMR (TMS standard, DMSO-D$_6$) 1.68$\gamma$, (pentuplet, 2.0, CH$_2$CH$_2$CH$_2$); 2.12 $\gamma$(triplet 4.0, CH$_2$CH$_2$CH$_2$) 4.97$\gamma$(singlet 1.0,=CH) 6.08 $\gamma$(multiplet,broad, 3.1,13 NH$_2$, =NH) 2.30* (singlet, CH$_3$—C$_6$H$_5$) 7.23* (multiplet, CH$_3$—C$_6$H$_5$).

* 10% toluene solvate

75 MHz $^{13}$C NMR (TMS reference, DMSO-D$_6$ solvent) with the following assignments:

21.68 $\gamma$, $^1$J=128.4, 1.0, C-5, 30.72 $\gamma$, $^1$J=126.9, 2.0, C-4, C-6, 96.15 $\gamma$, $^1$J=153.4, 1.0, C-2, 165.40 $\gamma$, 2 0, C-1, C-3.

Elemental Analyses: Experimental, %C=66.26, %H=8.78, %N=22.75 Calculated (assuming 10% toluene solvate), %C=67.40, %H=9.14, %N=23.47.

What is claimed is:

1. A method for preparing acid salts of 3-amino-2-cyclohexene-1-imine comprising the steps of:
   (a) partially hydrogenating a concentrated solution of m-phenylenediamine in acidic solution in the presence of a reduction catalyst selected from the group consisting of platinum, palladium and mixtures thereof wherein the catalyst is supported on a carrier selected from the group consisting of carbon, alumina, barium carbonate, steam activated peat carbon, and silica; at an elevated hydrogen pressure and at a temperature of about 25° C. to about 90° C.;
   (b) cooling the hydrogenation mass to about ambient temperature; and
   (c) removing the catalyst.

2. The method of claim 1 wherein the solvent is removed by evaporation to recover the acid salt of the compound 3-amino-2-cyclohexene-1-imine.

3. The method of claim 1 or claim 2 wherein the hydrogenation is carried out at a hydrogen pressure of about 50 to about 500 psig and a temperature of about 40° C. to about 60° C.

4. The method of claim 3 wherein the acid is 50-80% aqueous acetic acid or other carboxylic acids and is at least one equivalent of acid per mole of m-phenylenediamine.

5. The method of claim 3 wherein the acid is a mineral acid and is at least one equivalent of acid per mole of m-phenylenediamine.

* * * * *